US010470466B2

(12) United States Patent
Huang et al.

(10) Patent No.: US 10,470,466 B2
(45) Date of Patent: *Nov. 12, 2019

(54) ANTHROQUINONE CONTAINING DERIVATIVES AS BIOCHEMICAL AGRICULTURAL PRODUCTS

(71) Applicant: Marrone Bio Innovations, Inc., Davis, CA (US)

(72) Inventors: Huazhang Huang, Woodland, CA (US); Brian Campbell, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/995,437

(22) Filed: Jun. 1, 2018

(65) Prior Publication Data

US 2018/0295842 A1 Oct. 18, 2018

Related U.S. Application Data

(63) Continuation of application No. 15/168,597, filed on May 31, 2016, now abandoned, which is a continuation of application No. 12/897,776, filed on Oct. 4, 2010, now Pat. No. 9,380,778.

(60) Provisional application No. 61/248,878, filed on Oct. 5, 2009.

(51) Int. Cl.
| | |
|---|---|
| A01N 65/30 | (2009.01) |
| A01N 25/30 | (2006.01) |
| A01N 25/00 | (2006.01) |
| A01N 35/06 | (2006.01) |
| A01N 65/08 | (2009.01) |
| A01N 65/00 | (2009.01) |
| A01N 65/20 | (2009.01) |
| A01N 65/42 | (2009.01) |

(52) U.S. Cl.
CPC ............ *A01N 65/30* (2013.01); *A01N 25/00* (2013.01); *A01N 25/30* (2013.01); *A01N 35/06* (2013.01); *A01N 65/00* (2013.01); *A01N 65/08* (2013.01); *A01N 65/20* (2013.01); *A01N 65/42* (2013.01)

(58) Field of Classification Search
CPC ........ A01N 65/30; A01N 25/30; A01N 25/00; A01N 65/08; A01N 65/20; A01N 65/42; A01N 35/06; A01N 65/00
See application file for complete search history.

(56) References Cited

U.S. PATENT DOCUMENTS

| | | | |
|---|---|---|---|
| 3,726,850 A | 4/1973 | Detroit | |
| 3,813,236 A | 5/1974 | Allan | |
| 3,929,453 A | 12/1975 | Dimitri et al. | |
| 4,381,194 A | 4/1983 | Dellicolli et al. | |
| 4,602,004 A | 7/1986 | Cohen | |
| 4,612,051 A | 9/1986 | Miller et al. | |
| 4,666,522 A | 5/1987 | Hollis et al. | |
| 4,863,734 A | 9/1989 | Pommer et al. | |
| 5,300,521 A | 4/1994 | Eberle et al. | |
| 5,668,183 A | 9/1997 | Leuenberger | |
| 5,885,604 A | 3/1999 | Ballinger | |
| 5,989,429 A | 11/1999 | Bardinelli et al. | |
| 5,994,266 A | 11/1999 | Hobbs et al. | |
| 6,172,004 B1 | 1/2001 | Brinker et al. | |
| 7,241,439 B2 | 7/2007 | Jijakli et al. | |
| 7,344,730 B1 | 3/2008 | Stadler et al. | |
| 7,867,507 B2 | 1/2011 | Birthisel et al. | |
| 8,048,190 B2 | 11/2011 | Valencia | |
| 8,226,963 B2 | 7/2012 | Yang et al. | |
| 8,658,567 B2 | 2/2014 | Su et al. | |
| 8,889,197 B2 | 11/2014 | Su et al. | |
| 8,946,297 B2 | 2/2015 | Morita et al. | |
| 2004/0096428 A1 | 5/2004 | Jijakli et al. | |
| 2008/0193387 A1 | 8/2008 | Wolff | |

FOREIGN PATENT DOCUMENTS

| | | | |
|---|---|---|---|
| CN | 1387765 A | 1/2003 | |
| CN | 1515152 A | 7/2004 | |
| CN | 1961667 B | 4/2010 | |
| DE | 4411895 A1 | 5/1995 | |
| DE | 102007011676 A1 | 9/2008 | |
| EP | 173410 A1 | 3/1986 | |
| JP | 08099813 A | 4/1996 | |
| JP | 08109112 | 4/1996 | |
| JP | 2000033383 A | 2/2000 | |
| JP | 2000034202 A | 2/2000 | |

(Continued)

OTHER PUBLICATIONS

Krishnakumari et al., "Antifeedant activity of quinones from Ventilago madparaspatana," Fitoterapia 72:671-675 (2001).

(Continued)

*Primary Examiner* — Sarah Pihonak
*Assistant Examiner* — Jason Deck
(74) *Attorney, Agent, or Firm* — Chainey P. Singleton; Ying-Horng Liu

(57) ABSTRACT

Formulations containing anthraquinone derivatives derived from root of *Reynoutria sachalinensis* with increased effectiveness as pesticides are provided. These formulations may comprise (a) a preparation comprising one or more anthraquinone derivatives derived from root of *Reynoutria sachalinensis* having activity against plant pests; (b) one or more C2-C7 alcohols, or glycols or lactones; and (c) one or more surfactants selected from the group consisting of a sulfate, ethoxylated fatty acid esters wherein said alcohols and surfactants are present in amounts effective to stability said preparation. Also provided are methods of using these formulations as pesticides.

11 Claims, No Drawings

(56) References Cited

FOREIGN PATENT DOCUMENTS

| WO | 1998011782 A1 | 3/1998 |
|---|---|---|
| WO | 9932205 A1 | 7/1999 |
| WO | 2003005816 A1 | 1/2003 |
| WO | 2004000014 A1 | 12/2003 |
| WO | 2005010315 A2 | 2/2005 |
| WO | 2006015865 A1 | 2/2006 |
| WO | 2006037632 A1 | 4/2006 |
| WO | 2006037633 A1 | 4/2006 |
| WO | 2006037634 A1 | 4/2006 |
| WO | 2007094533 A1 | 8/2007 |
| WO | 2010040834 A2 | 4/2010 |

OTHER PUBLICATIONS

Kuc et al., "Development and future direction of induced systemic resistance in plants," Crop Protection 19:859-861 (2000).
Lehnof, "A Reynoutria sachalinensis based plant extract for preventive control of powdery mildew," Biofs. esp. pp. 5, 7, 8, 11, 14, and 15 (2007).
Limpel et al., "Weed control by Dimethyl tetrachloroterephthalate alone and in certain combinations," N.E. Weed Control Conference 16:48-53 (1962).
Lin et al., "Micropropagation of Polygonum multifloras THUNB and Quantitative Analysis of the Anthraquinone Emotion and Physician Forms in in Virtro Propagated Shoots and Plants," Biol. Pharm. Bull. 26(10); pp. 1467-1471 (Oct. 2003).
Liu et al., "Anthraquinone in Rheum palmate and Rumex dentatus (Polygonaceae), and phorbol esters in Jatropha curvas (Euphorbiaceae) with molluscicidal activity against the schistosome vector snails Oncomelania, Biomphalaria and Bulinus," Tropical Medicine and International Health 2:179-188 (1997).
May, "Evolution of pesticide resistance," Nature 315:12-13 (1985).
McCutcheon's vol. 1: Emulsifiers & Detergents, North American Edition, expert provided (2002).
McGrath, "Fungicide resistant in cucurbit powdery mildew: Experiences and challenges," Plant Disease 85:236-245 (2001).
McGrath, "Guidelines for managing cucurbit powdery mildew in 2006," Cornell University, Vegetable MD Online (2006).
McGrath, "Occurrence of strobilurin resistance and impact on managing powdery mildew on cucurbits," Cornell University; Vegetable MD Online (2003).
Muravieva, "Meditsina," 1978 (Russian original).
Muravieva, "Meditsina," English translation (1978).
Nash, "Phytotoxic Interaction Studies—Techniques for Evaluation and Presentation of Results," Weed Science 29:147-155 (1981).
Penncozeb® 80 WP fungicide. Group M Fungicide—label and booklet 2008 (Pest Management Regulatory Agency label transcript service) Pesticide Alert, Strawberry News Bulletin—Cabrio for use on strawberries. 2003 (English and Spanish documents).
Pesticide Alert, Strawberry News Bulletin—Cabrio for use on strawberries. 2003 (English and Spanish documents).
Quarles, "Giant Knotweed, Plant Disease Protection, and Immortality," The IPM Practitioner, Monitoring the Field of Pest Management; vol. XXXI, No. 3/4; pp. 1-6; Mar./Apr. 2009.
Randoux et al., "Inhibition of Blumeria gram inis f. sp. tritici Germination and Partial Enhancement of Wheat Defenses by Milsana" Phytopathology 96:1278-1286 (2006).
Regalia® Bioprotectant Concentrate—Label—May 2009.
Regalia® SC a Powerful New Tool for Powdery Mildew Control on Cucurbits—May 2009 (fact sheet 2).
Reglia® SC a powerful New Tool for Powdery Mildew, Downy Mildew and Gummy Stem Blight on Cucurbits—May 2009 (fact sheet 1).
Reuveni, "Improved control of powdery mildew (Sphaerotheca mannose) of nectarines in Israel using strobilurin and polyoxin B fungicides; mixture with sulfur; and early bloom applications," Crop Protection 20:663-668 (2001).
Richer, "Synergism—a patent view," Pesticide Science 19:309-315 (1987).
Ross, "Systemic acquired resistance induced by localized virus infections in plants," Virology 14:340-358 (1961).
Saleh et al., Flavonoids and Anthraquinones of some Egyptian Rumex Species (polygonaceae); Bioch. Systematics and Ecology, vol. 1, No. 2, pp. 301-303 (1993).
Schmitt et al., "Biocontrol of plant pathogens with microbial BCAs and plant extracts—advantages and disadvantages of single and combined use," Modern fungicides and anti fungal compounds IV; Proceedings of the 14th International Reinhardsbrunn Symposium 2004, BCPC, Atlon, UK, pp. 205-225 (2005) (abstract only submitted).
Schmitt, "Induced responses by plant extracts from Reynoutria sachalinensis: a case study," Bull. IOBC/WPRS 25:83-88 (2002).
Schmitt, "Use of Reynoutria sachalinensis plant extracts, clay preparations and Brevibacillus brevis against fungal diseases of grape berries," Fordergeneinschaft Okologisher Ostbau e.V. (FOKO) and der Staatlichen Lehr—und Versuchsanstalt fur Wein—und Obslbau (LvWO) Weinbarg; 10th International conference on cultivation technique and phytopathological problems in organic fruit-growing and viticulture; preparations at the meeting from 04-07-02-2002, Weinsberg, Germany, pp. 146-151 (2002).
Schnabel et al., "Reduced sensitivity in Monilinia fructicola to propiconazole in Georgia and implications for disease management," Plant Disease 88:1000-1004 (2004).
Singh et al., "Antifungal anthraquinone from Saprosma fragrans," Bioorganic and Medicinal Chemistry Letters 16:4512-4514 (2006).
Su, "Sporulation of uremia lactucae affected by temperature, relative humidity, and wind in controlled conditions," Phytopathology 94:396-401 (2004).
Subash et al., "Determination and location variations in the quantity of hydroxyanthraquinones and their glycosides in rhizomes of Rheum emoji using high-performance liquid chromatography," J. Chromatography A, 1097:5-65 (2005).
Supplemental European Search Report in EP App. No. 10805012.1 dated Dec. 13, 2013, 11 pages.
Tamokou et al., "Antimicrobial activities of methanol extract and compounds from stem bark of Vismia rubescens," J. Ethnopharmacol, 124:571-575 (2009).
Third Party Observations against EP Patent App. No. 10805012.1.
Tiebre et al., "Hybridization and sexual Reproduction in the Invasive Alien Fallopia (Polygonaceae) Complex in Belgium," Annals of Botany 99:193-203 (2007).
Van Den Bosch et al., "Models of fungicide resistance dynamics," Annual Review of Phytopathology 46:123-147 (2008).
Van Loon et al., "Systemic resistance induced by rhizosphere bacteria," Annual Review of Phytopathology 36:453-483 (1998).
Vechet et al., "A comparative study of the efficiency of several sources of induced resistance to powdery mildew (Blumeria gram inis f. sp. tritici) in wheat under field conditions," Crop Protection 28:151-154 (2009).
Vrchotova et al., "Allelopathic properties of knotweed rhizone extracts," Plant Soil Environ., 45, 2008 (7):301.303.
Vrchotova et al., "The Stilbene and Catechin Content of the Spring Sprouts of Reynoutria Species," Acta Chromatographica, 19:21-28 (2007).
Walters et al., "Induced resistance for plant disease control: maximizing the efficacy of resistance elicitors," Phytopathology 85:1368-1373 (2005).
Werner et al., "Anthraquinone-based bird repellent for sunflower crops," Applied Animal Behaviour Science 129 (2-4):162-169 (2011).
Wurms et al., "Effects of Milsana and Benzothiadiazole on the ultrastructure of powdery mildew haustoria in cucumber," Phytopathology 89:728-736 (1999).
Wyenandt et al., "Fungicide resistance management guidelines for cucurbit downy and powdery mildew control in the mid-Atlantic and Northeast regions of the US," Phytopathology 99 (2009 APS Annual Meeting Abstracts of Presentations) S144-S144 (2009).
Yang et al., "Synergistic interaction of physician and chrysophanol on plant powdery mildew," Pest Management Sci 63:511-615 (2007).

(56) References Cited

OTHER PUBLICATIONS

Zhang et al., "Antioxidant Activity of Anthraquinone and Flavonoids from Flower of Reynoutria sachalinensis," Arch Pharm Res vol. 28, No. 1, 22-27 (2005).
"Rheum palm alum and Rheum rhabarbarum," Internet Archive Date: May 19, 2000 [Retrieved from the Internet on Mar. 9, 2012]; Retrieved from the Internet at http://web.archive.org/web/20000519232753/http://www.ansci.cornell.edu/plants/mecidina/rhub.html>.
Samoucha et al., "Synergy between metalaxyl and mancozeb in controlling downy mildew in cucumbers," Phytopathology 74:1434-1437 (1984).
Agarwal et al., "Antifungal Activity of Anthraquinone Derivatives from Rheum Emodi," J. Ethnopharmacol., 72:43-46 (2000).
Bardin et al., "Compatibility Between Biopesticides Used to Control Grey Mold, Powdery Mildew and Whitefly on Tomato," Biological Control 46, 476-483 (2008).
Bartlett et al., "The Strobilurin Fungicides," Pest Management Science 58:649-662 (2002).
Belanger et al., "Challenges and Prospects for Integrated Control of Powdery Mildews in the Greenhouse," Canadian Journal of Plan Pathology 19:310-314 (1997).
Bokshi et al., "A Single Application of Milsana Followed by Bio. Assists in the Control of Powdery Mildew in Cucumber and Helps Overcome Yield Losses," Journal of Horticultural Science and Biotechnology 83:701-706 (2008).
Braun et al., "The taxonomy of the powdery mildew fungi. In the powdery mildews: a comprehensive treatise," R. Belanger, W.R. Bushness, A.J. Did and T.L.W. Carver. Eds. St. Paul, MN, APS Press: 13-55 (2002).
Bravo Fungicide draft, 10-1000L Draft Label Text Container—Apr. 2009.
Burpee, L and R, "Reassessment of fungicide synergism for control of dollar spot," Plant Disease 92:601-606 (2008).
Captan, General Fact Sheet National Pesticide Information Center (2002).
Daayf, F. et al., "The effects of plant extracts of Reynoutria sachalinensis on powdery mildew development and leaf physiology of long English cucumber," Plant Disease 79:577-580 (1995).
Dewaard, "Synergism and antagonism in fungicide mixtures containing sterol demethylalion inhibitors," Phytopathology 86: 1280-1283 (1996).
Dow AgroSciences Nova TM 40W Agricultural Fungicide—Material Safety Data Sheet—Mar. 2009.
Durrant et al., "Systemic acquired resistance," Annual Review in Phytopathology 42:185-209 (2004).
Evonik Industries Additives for Pesticides Formulation; Apr. 2008.
Examination Report, New Zealand Patent App. No. 599664, dated Nov. 29, 2012, corresponding to U.S. Appl. No. 12/987,776.
F&N Tests Report No. 55:25—publication date 1999.
F&N Tests Report No. 55:353—publication date 1999.
F&N Tests Report No. 56:V76—publication date 2000.
F&N Tests Report No. 57:V086—publication date 2001.
F&N Tests Report No. 58:V024—publication date 2002.
F&N Tests Report No. 58:V082 0 publication date 2002.
F&N Tests Report No. 59:089—publication date 2003.
F&N Tests Report No. 59:SMF029—publication date 2003.
F&N Tests Report No. 59:V004—publication date 2003.
F&N Tests Report No. 59:V135—publication date 2003.
F&N Tests Report No. 60:V137—publication date 2004.
Federal Register, vol. 70, Issue 182 (Wednesday, Sep. 21, 2005).
Fofana et al., "Milsana R-induced resistance in powdery milder-infected cucumber plants correlates with the induction of chalcone synthase and chalcene isomerase," Physiol. ole. Plant Pathology., 61, 121-132 (2002).
Fraaije et al., "Qol resistance development in populations of cereal pathogens in the UK," BCPC International Congress Crop Science and Technology, Alton, Wants, UK, pp. 689-694 (2003).
Fungicide Elevate® 50 WDG; Aug. 2007 (French language document).
Gisi, "Synergistic interactions of fungicides in mixtures," Phytopathology 86:1273-1279 (1996).
Hafez et al., "The side-effects of plant extracts and metabolites of Reynoutria sachalinensis (F. Schmidt) Nakai and conventional fungicides on the beneficial organism Trichogramma cacoeciae Marchal (Hym., Trichogrammatidae)," Journal of Applied Entomology 123:363-368 (1999).
Holb et al., "The benefits of combining elemental sulfur with a DMI fungicide to central Monilinia fructicola isolates resistant to propiconazole," Pest Management Science 64:156-164 (2008).
Horst et al., "Effect of sodium bicarbonate and oils on the control of powdery mildew and black spot on roses," Plant Disease 76:247-251 (1992).
Hwang et al., "Effect of see treatment and root pathogens on seeking establishment and yield of alfalfa, birdsfoot trefoil and sweet clover," Plant Pathology Journal 5:322-328 (2006).
International Preliminary Report on Patentability dated Feb. 9, 2012 for counterpart International App. Ser. No. PCT/US2010/043612.
International Preliminary Report on Patentability dated Apr. 19, 2012 for counterpart PCT App. Ser. No. PCT/US2010/051359.
International Search Report (partial search) and Invitation to Pay Fees for Additional Search dated May 2, 2011 in counterpart PCT App. No. PCT/US2010/043612.
International Search Report and Written Opinion dated Jun. 24, 2011 from counterpart PCT App. No. PCT/US2010/051359.
International Search Report and Written Opinion dated Jul. 29, 2010 in counterpart PCT App. No. PCT/US2010/43612.
International Search Report dated May 24, 2012 from counterpart PCT App. No. PCT/US2012/123571.
International Search Report dated Jun. 29, 2012 from counterpart PCT App. No. PCT/US2011/59197.
Izahi, "Emodin-Asecondary Metabolite with Multiple Ecological Functions in Higher Plants," New Phytologist 105:205-217 (2007).
James, "A manual assessment keys for plant diseases," Key Nos. 2.2 and 2.4, American Phytopathological Society, St. Paul, MN (1971).
Jin et al., "Cytotoxic Anthraquinone and Stilbene from Reynoutria sachalinensis (Fr. Schm.) Nakai," Korean Journal Medicinal Crop Sci., vol. 32, No. 2, pp. 80-84 (Mar. 2005).
Karaoglanidis et al., "Efficacy of strobilurins and mixtures with DMI fungicides in controlling powdery mildew in field-grown sugar beet," Crop Protection 25:977-983 (2006).
Kong et al., "Inhibition of MAO A and B by some plant-derived alkaloids, phenols and anthraquinone," J. Ethnopharmacology 91:351-355 (2004).
Konstantinidou-Doltsinis et al., "Control of powdery mildew of grape in Greece using Sporodex Land Milsana," Journal of Plant Diseases and Protection 114:256-262 (2007).
C. Avila-Adame et al.; "MOI-106: A new alternative for controlling fungal plant pathogens in ornamentals and edible crops"; vol. 98, No. 6, p. S16, Phytopathology Jun. 2008.

ANTHROQUINONE CONTAINING DERIVATIVES AS BIOCHEMICAL AGRICULTURAL PRODUCTS

CROSS-REFERENCE TO RELATED APPLICATIONS

This application is a Continuation and claims priority based on U.S. patent application Ser. No. 15/168,597, field May 31, 2016, which is a Continuation and claims priority based on U.S. patent application Ser. No. 12/897,776, filed Oct. 4, 2010 (issued as U.S. Pat. No. 9,380,778), which claims priority to U.S. Provisional Application Ser. No. 61/248,878, filed Oct. 5, 2009, the contents of each of which are incorporated by reference herein in their entireties.

TECHNICAL FIELD

Disclosed herein are compositions and methods for formulating preparations containing anthraquinone derivatives (e.g., physcion, emodin, chrysophanol, and ventiloquinone so on) as biopesticides.

BACKGROUND OF THE INVENTION

With the rapid spread of resistance of plant pathogen populations to synthetic fungicides and increased awareness of human to environmental pollution, an alternative means of control plant diseases is very necessary. The most effective means is to boost the plant defense mechanisms by induced plant resistance [L. C. van Loon, P. A. H. M. Bakker, and C. M. J. Pieterse, Systemic resistance induced by Rhizosphere bacteria, Annu. Rev. Phytopathol. 1998. 36:453-83] and/or systemic acquired resistance [W. E. Durrant and X. Dong, Systemic acquired resistance, Annu. Rev. Phytopathol., 2004, 42:185-209]. Therefore, reducing and/or delaying the formation of pathogen resistance and protecting environments.

Induced resistance is a state of enhanced defensive capacity developed by a plant when appropriately stimulated [Kuc, J., Development and future direction of induced systemic resistance in plants, Crop Protection, 2000, 19, 859-861]. Induced plant resistance can be triggered by chemicals, nonpathogens, avirulent forms of pathogens. When induced resistance is systemic, it is commonly referred as systemic required resistance [L. C. van Loon, P. A. H. M. Bakker, and C. M. J. Pieterse, Systemic resistance induced by Rhizosphere bacteria, Annu. Rev. Phytopathol. 1998. 36:453-83].

Anthraquinone derivatives such as rhein, emodin, aloe-emodin, parietin, physcion, emodin-glycoside, physcion-glycoside, chrysophanol and chrysophanol-glycoside as well belong to one family of chemicals which induce plant resistance to pathogens. Induced resistance of this class of chemicals was well studied by using MILSANA® biofungicide, the commercial name given to the extract of giant knotweed [B. Fofana, D. J. McNally, C. Labbe, R. Boulanger, N. Benhamou, A. Seguin, R. R. Belanger, MILSANA® biofungicide induced resistance in powdery mildew-infected cucumber plants correlates with the induction of chalcone synthase and chalcone isomerase, Physiol. Molec. Plant Pathol. 2002, 61, 121-132]. Physcion and emodin are the major bioactive anthraquinone derivatives in MILSANA® biofungicide that is verified in our laboratory by bioassay-guided fractionation. Glycoside derivatives of physcion and emodin are the minor for the activity. Numerous other studies in the agricultural field have shown that many anthraquinone derivatives displayed strong bioactivities such as antifungal, antifeedant, antimicrobial, molluscicidal activity [S. K. Agarwal, S. S. Singh, S. Verma, S. Kumar, Antifungal activity of anthraquinone derivatives from Rheum emodi, J. Ethnopharmacol. 72 (2000) 43-46S; J. D. D. Tamokoua, M. F. Tala, H. K. Wabo, J. R. Kuiatea, P. Tane, Antimicrobial activities of methanol extract and compounds from stem bark of Vismia rubescens, J. Ethnopharmacol, 2009, in press; G. N. Krishnakumari, B. Bhuvaneswari, I. R. Swapna, Antifeedant activity of quinones from Ventilago madaraspatana, Fitoterapia, 72 (2001) 671-675; Y. Liu, F. Sporer, M. Wink, J. Jourdane, R. Henning, Y. L. Li and A. Ruppel, Anthraquinones in Rheum palmatum and Rumex dentatus (Polygonaceae), and phorbol esters in Jatropha curcas (Euphorbiaceae) with molluscicidal activity against the schistosome vector snails Oncomelania, Biomphalaria and Bulinus, Tropical Medicine and International Health, 1997, 2(2), 179-188]. Synergism also exists in the interaction of these compounds such as in the interaction between physcion and chrysophanol [X-J., Yang, L-J., Yang, S-N., Wang, D-Z., Yu, H-W., Ni, Synergistic interaction of physcion and chrysophanol on plant powdery mildew, Pest Manag Sci 63:511-515 (2007)].

To protect the environments, MILSANA® biofungicide, a product derived from Reynoutria sachalinensis, was formulated as a water-based Suspension Concentrate (SC), registered as a biochemical pesticide (U.S. Pat. No. 4,863, 734 Process for combating fungi; U.S. Pat. No. 5,989,429, Processes for forming stabilized biochemical agricultural products). MILSANA® biofungicide is a very effective product for the control of mildew. However, two of the major problems that prevent it as a good commercial pesticide product are industrial reproducibility and the instability of the formulation. Reproducibility of making such a formulation is poor in industry. Because many chemicals in the extracts such as chlorophylls and anthraquinone derivatives are hydropbobic compounds, these compounds can aggregate together to form bigger particles as time passes by. Multiple difficulties are associated with such large particles. They are difficult to dissolve in water. Additionally, effective concentration of active ingredients in the application solution is decreased, resulting in worse efficacy; the big particles also can stick to the spraying containers and it is difficult to wash away with water. The big particles can even block the nozzles.

BRIEF SUMMARY OF THE DISCLOSURE

Disclosed herein are formulations of anthraquinone derivatives as biochemical agricultural products for use against plant pests, particularly plant phytopathogens such as plant pathogenic bacteria, fungi, insects, nematodes and/or as a molluscicide, as well as the use of pre- and post-emergence herbicide against weeds. In a particular embodiment, the anthraquinone derivative (s) used in compositions and methods disclosed herein is (are) the major active ingredients or one of the major active ingredients.

In particular, provided is a formulation comprising (a) a preparation comprising one or more anthraquinone derivatives having activity against plant pests; (b) one or more C2-C7 aliphatic alcohols or glycols and lactones, (c) one or more surfactants selected from the group consisting of a sulfate, ethoxylated fatty acid esters and optionally at least one of an antifreeze or a carrier which may be used to modulate phytopathogenic infection in a plant. The formulation may be in the form of a liquid (concentrate or ready to use), emulsion or solid.

In a particular embodiment, the formulation comprises a preparation comprising one or more anthraquinone derivatives having activity against plant pests dissolved in hexanol and ethanol and further comprises sodium lauryl sulfate and calcium propionate. The anthraquinone derivative may be present in an amount of about 0.001% to 45%, hexanol may be present in the amount of about 0.1% to 10%, ethanol may be present in the amount of about 0.1% to 20%, sodium lauryl sulfate may be present in the amount of about 0.01% to 15%, and calcium propionate may be present in the amount of about 0.001% to 10%.

In yet another particular embodiment, the formulation comprises (a) a preparation comprising one or more anthraquinone derivatives having activity against plant pests: (b) hexanol; (c) sodium lauryl sulfate; (d) 2-[2-[3,4-bis(2-methoxyethoxy)oxolan-2-yl]-2-(2-methoxyethoxy)ethoxy] ethyl hexadecanoate; (e) calcium propionate; (f) propylene glycol and (g) water and is optionally in the form of a microemulsion. The preparation of (a) may be present in an amount of about 0.001% to 45%, hexanol is present in the amount of about 0.1-10%, 2-[2-[3,4-bis(2-methoxyethoxy)oxolan-2-yl]-2-(2-methoxyethoxy)ethoxy)]ethyl hexadecanoate is present in the amount of 0.1-35%, propylene glycol is present in the amount of about 1% to 8%, sodium lauryl sulfate is present in the amount of about 0.01% to 15% and calcium propionate is present in the amount of about 0.001% to 10%. The invention further provides an aqueous formulation comprising (a) a preparation comprising one or more anthraquinone derivatives having activity against plant pests; (b) one or more bases; (c) one or more water miscible co-solvents. The preparation of (a) may be present in an amount of about 0.01-45% by weight; the base is present in an amount of about 0.1-10%; the co-solvent is present in the amount of 0.1% to 30%.

In a particular embodiment, the formulation comprises said derivative, a glycol (e.g., propylene glycol), an organic acid (e.g., formic acid), a base (e.g., sodium hydroxide or sodium carbonate). The preparation may be present in an amount of about 0.01 to about 45% by weight; the base is present in an amount of about 0.1% to 5%; propylene glycol is present in the amount of about 0.1% to 8% and organic acid is present in the amount of about 0.1% to 5%.

In a particular embodiment, formulations include but are not limited to water-based formulations such as suspension concentration (SC), microemulsion (ME), nanoemulsion (NE), soluble liquid (SL), ready-to-use (RTU), emulsion in water (EW), microencapsulated or nano-encapsulated formulations. It also includes oil-based formulations such as emulsifiable concentrate (EC), and powder formulations such as water-soluble powder (WSP), water dispersible granules (WDG) or water dispersible tablets (WGT).

In yet another particular embodiment, the formulation further comprises an antimicrobial agent which may be a chemical pesticide and/or biopesticide.

Also provided are methods of using the formulations set forth hereinabove for modulating phytopathogenic infection (e.g., fungus or bacteria) in a plant comprising applying to the plant and/or seeds thereof and/or substrate used for growing said plant an amount of the formulations disclosed herein effective to modulate said phytopathogenic infection.

The use of (a) a preparation comprising one or more anthraquinone derivatives having activity against plant pests; (b) one or more C2-C7 aliphatic alcohols, or C2-C7 glycols or C2-C7 lactones and (c) one or more surfactants selected from the group consisting of a sulfate for the preparation of a formulation for use against plant pests or alternatively use of (a) a preparation comprising one or more anthraquinone derivatives having activity against plant pests; (b) one or more bases; (c) one or more water miscible co-solvents for the preparation of a formulation for use against plant pests is provided.

In a particular embodiment, provided are methods of using the formulations set forth hereinabove to modulate infestation of plant pests in soil by applying to the soil an amount of the formulations set forth hereinabove effective to modulate said plant pest infestation.

The formulations set forth above and disclosed herein can be used simultaneously with an anti-microbial agent such as a biopesticide or chemical pesticide in a tank mix or in a program (sequential application called rotation) with predetermined order and application interval during the growing season. Thus, also provided is a combination comprising the formulation set forth above and the anti-microbial agent.

Alternatively, the formulations set forth above may further comprise an anti-microbial agent. In a particular embodiment, the antimicrobial agent is present in the amount of about 0.001% to about 10% by weight.

Formulations and combinations comprising the ingredients set forth above as well as anti-microbial agents may also be used to modulate infestation of plant pests on plants and/or soil and modulating phytopathogeic, fungal and bacterial infection.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a." "and" and "the" include plural references unless the context clearly dictates otherwise. For example, "a fungus" also encompasses "fungi".

As defined herein, the term "modulate" is used to mean to alter the amount of phytopathogenic, bacterial or fungal infection, plant pest infestation or rate of spread of phytopathogenic bacterial or fungal infection or plant pest infestation.

Anthraquinone Derivatives

Anthraquinone derivatives include but are not limited to physicion, emodin, chrysophanol, ventiloquinone, emodin glycoside, chrysophanol glycoside, physcion glycoside, 3,4-dihydroxy-1-methoxy anthraquinone-2-corboxaldehyde, damnacanthal. These derivatives share a similar structure as follows:

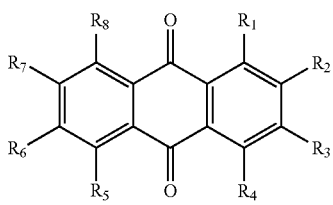

Where R1, R2, R3, R4, R5, R6, R7 and R8 are hydrogen, hydroxyl, hydroxylalkyl, halogen, carboxyl, alkyl, alkyoxyl, alkenyl, alkenyloxyl, alkynyl, alkynyloxyl, heterocyclyl, aromatic, or aryl group, sugars such as glucose;

In a particular embodiment, the invention is directed to anthraquinone derivatives that are contained in extracts derived from plant families including but not limited to Polygonaceae, Rhamnaceae, Fabaceae, Asphodelaceae, and Rubiaceae. These compounds can be isolated or obtained from any part of plants such as leaf, stem, bark, root and fruits. Plant materials can be wet and dry, but preferably dry plant materials. To meet the biochemical agricultural products, solvents and processes that are used in the extraction and purification must meet the requirements of National Organic Program (NOP) [www.ams.usda.gov/AMSv1.O/nop, cited on Jul. 20, 2009].

In a more particular embodiment, the plant extract is derived from a member of the Polygonaceae family. As defined herein, "derived from" means directly isolated or obtained from a particular source or alternatively having identifying characteristics of a substance or organism isolated or obtained from a particular source. In a particular embodiment, extract in said combination contains at least one anthraquinone derivative such as physcion and optionally emodin. Members of the Polygonaceae family include but are not limited to Acetosella, Antigonon, Aristocapsa, Bilderdykia, Brunnichia, Centrostegia, Chorizanthe, Coccoloba, Coccolobis, Coccolobo, Corculum, Dedeckera, Delopyrum, Dentoceras, Dodecahema, Emex, Eriogonum, Fafopyrum, Fagopyrum, Fallopia, Gilmania, Goodmania, Harfordia, Hollisteria, Koenigia, Lastarriaea, Mucronea, Muehlenbeckia, Nemacaulis, Oxyria, Oxytheca, Perscarioa, Persicaria, Pleuropterus, Podopterus, Polygonella, Polygonum, Pterostegia, Rheum, Rumex, Ruprechtia, Stenogonum, Systenotheca, Thysanella, Tovara, Tracaulon, Triplaris and even more particular embodiment, the extract may be derived from a *Reynoutria* (alternately referred to as *Fallopia*) sp or *Rheum* species. In a most particular embodiment, the extract is derived from *Reynoutria sachalinensis*.

In yet a more particular embodiment, percent concentration of anthraquinone derivatives in these formulations follows a range of between 0.001 to 99.99%. In a specific embodiment, the concentration range is between about 0.01 to 95%. The concentration is preferably between about 0.01% to about 45%.

Anthraquinone derivatives naturally exist in some plants, fungi, lichens, and insects. As noted above, in plants, they are present the different families such as Polygonaceae, Rhamnaceae, Fabaceae, Asphodelaceae, Rubiaceae and others [Subash C. Verma, Narendra P. Singh, Arun K. Sinha, Determination and locational variations in the quantity of hydroxyanthraquinones and their glycosides in rhizomes of *Rheum emodi* using high-performance liquid chromatography, *Journal of Chromatography A*, 1097 (2005) 59-65]. Anthraquinone derivatives widely distribute different plant tissues such as leaf, stem, bark, root and fruits. Physcion, as an example, exists in many herbs such as Chinese gooseberry (or Kiwi fruit, *Actinidia chinensis* Planch), *abrus* herb (*Abrus Cantoniensis* Hance), shan ma gen (*Boehmeria tricuspis* Hance), coffee senna seed (*Cassia occidentalis* L.), *cassia* seed (or seed of sickle senna *Cassia obtusifolia* L.), senna leaf (*Cassia angustifolia* Vahl.), leaf of ringworm senna (*Cassia alata* L.), common dysosmatis rhizome and Root (*Dysosma versipellis* Hance), bai ba jiao lian (*Dysosma majorensis* Gagnep.), herb of tree clubmoss (*Lycopodium obscurum* L.), medicinal indian mulberry(*Morinda officinalis* How), root of thatch screwpine (*Pandanus tectorius* Soland), he shou wu (*Polygonum multiflorum* Thunb), ji xue qi (*Polygonum amplexicaule*), xue san qi (*Rheum likiangense* San.), xi zang suan mo (*Rumex patientia* L.), mao mai suan mo (*Rumex gmelini* Turcz.), niu she cao (*Rumex dentatus* L.), suan mo (*Rumex acetosa* L.), hu zhang (*Polygonum Cuspidatium*), to da huang (*Rumex obtusifolius* L.), to huang (*Rheum nodile* Hook.), yang ti (*Rumex japonicus* Houtt.), root of oriental buckthorn (*Rhamnus crenata* Sieb.), qian cao (*Rubia cordifolia* L.), da feng yao (*Rhamnus napelensis* Wall.), stem of sargentgloryvine (*Sargentodoxa cuneata* Oliv .), snow lotus herb (*Saussurea laniceps* Hand.) and so on [Chinese herb database www.tcmlib.com/ cited on Jul. 20, 2009].

Anthraquinone derivatives can be extracted from plant materials by any inorganic or organic solvents which are allowed to use by National Organic Programs [www.ams.usda.gov/AMSv1. O/nop, cited on Jul. 20, 2009]. For example, these materials can be ground and then extracted with a base solution, then acidified by an acid solution and finally extracted by organic solvents such as ethyl acetate, butanol; or ground materials can be directly extracted with organic solvents such as ethanol, or ethyl acetate; or any other method and their combination to extract anthraquinone derivatives from plant materials. The extraction solution is then concentrated or dried under vacuum with an appropriate temperature such as 20-100° C., preferred to 30-70° C.

Formulations

Depending on extraction methods, extracts containing anthraquinone derivatives may include from very water soluble compounds (e.g., free sugars, glycosides, acids, amine acids and others) to very hydrophobic compounds (e.g., chlorophylls, long chain fatty acids, anthraquinone derivatives and others). The physical properties of these extracts may lead to problems for traditional oil-based formulations because hydrophilic compounds cannot dissolve in oil, but in water, and hydrophobic compounds cannot dissolve in water, but in oil. In addition, limited oils are allowed for organic farming [www.ams.usda.gov/AMSv1. O/nop, cited on Jul. 20, 2009]. Only extracts which was extracted with hydrophobic solvents such as ethyl acetate or butanol are suitable for oil-based formulations such as emulsifiable concentrate (EC). Therefore, powder and water-based formulations are the best choice for any extracts. Water-based formulations include suspension concentration (SC), microemulsion (ME), nanoemulsion (NE), soluble liquid (SL), emulsion in water (EW), ready-to-use (RTU) and microencapsulate or nano-encapsulate formulation. Powder formulations include but are not limited to water soluble powder (WSP), water dispersible granules (WDG) and water dispersible tablet (WGT). To easily compare with MILSANA® SC biofungicide, dry ethanol extract powders of giant knotweed *Polygonum sachalinense* is used in all following formulation examples.

Suspension Concentrate

Suspension concentrate (also referred to as "SC") is defined as a stable suspension of solid particulate active ingredients in a liquid intended for dilution with water before use. The formulation may contain active ingredient, antifreeze, dispersant, stabilizer, water and others such as antimicrobial, antifoaming ingredients.

Physcion and emodin are the major technical active ingredients in dry ethanol extract powders of giant knotweed *Polygonum sachalinense*. Their melting points are over 200° C. and they are very stable in water. Therefore, based on active ingredients, knotweed ethanol extract is suitable for SC formulation.

Water-miscible organic solvents could help to dissolve some of hydrophobic compounds and solved problems about the aggregation or big particles. Basically, all water-miscible solvents from allowed substance lists in NOP [www.ams.usda.gov/AMSv1.O/nop, cited on Jul. 20, 2009] is possible unless phytotoxicity is shown at the highest recommended application rate. Such solvents include but are not limited to alcohols, which may include but are not limited to C2-C7 aliphatic alcohols (e.g., ethanol, isopropanol, glycols (e.g., propylene glycols), acids (e.g., acetic acid, propanoic acid) and lactones (e.g., gamma-butyrolactone). The maximal percent content of the watermiserable organic solvent in SC should allow maximal hydrophobic compounds to dissolve, but not produce phytotoxicity at the highest recommended application rate. The active ingredient in such a formulation follows a range of 0.001% to 90%, preferably 0.01% to 45%.

The preparation may be optimized by adjusting ethanol amount. Percent weight of ethanol was investigated at 1, 2, 4, 6, 8 and 10% in the final formulation. Based on physical properties of final formulations such as suspended particle size and precipitation, the formulation with 10% (W/W) ethanol was the best formulation.

Microemulsions

A microemulsion (also referred to as "ME") is a thermodynamic stable emulsion that is clear because the individual droplets of the dispersed phase are less than 100 nanometers in diameter. The composition of ME generally consists of active ingredients, antifreeze, co-solvent, surfactants, water and others such as antimicrobial agents. The active ingredient(s) for such a formulation is (are) within a range of 0.1-50%, preferably 1-30%.

Antimicrobial agents can prevent microorganisms from growing in the ME during storage. Any chemical listed in allowed substance in NOP [www.ams.usda.gov/AMSv1. O/nop, cited on Jul. 20, 2009] is suitable for such purpose. For example, bicarbonate salts, carbonate salts, propionate salt, sorbate salt, benzoate and so on. The amount of the antimicrobial agents follows a range of 0.1 to 15%, preferably 2-10%. The antimicrobial agent may be a chemical pesticide and in particular may a multi-site noninorganic, chemical fungicide selected from the group consisting of chloronitrile, quinoxaline, sulphamide, phosphonate, phosphite, dithiocarbamate, chloralkythios, phenylpyridin-amine, cyano-acetamide oxime. Alternatively, the chemical pesticide may be an insecticide or antibacterial agent that includes but is not limited to carbamates, organophosphates, cyclodiene organochlorides, phenylpyrazoles, pyrethroids, pyret-rins, neonicotinoids, nitroguanadines, nicotine, Spinosyn, glycosides, juvenile hormone analogues and other insect growth regulators, pyridine azomethine, pyridine carboxamide, tetrazine, thiazolidinone, 2,4-diphenyloxzoline derivatives, organotin, pyrrole, buprofezin, hydramethylnon, naphtoquinon derivatives, pyridazinone, phenoxypyrazole, tetronic acid, carbazate, rotenone, organochlorinediphenylaliphatics. The antimicrobial agent may be a biopesticide derived from a microorganism such as *Streptomyces, Burkholderia, Trichoderma, Gliocladium* or may be a natural oil or oil-product having fungicidal and/or insecticidal activity (e.g., paraffin oil, tea tree oil, lemongrass oil).

Antifreezes are generally alcohols (e.g., isopropanol, butanol, glycerin or glycols such as propylene glycol), and sugars (e.g., glucose), which are listed in allowed substance in NOP [http://www.ams.usda.gov/AMSv1. O/nop, cited on Jul. 20, 2009]. However, antifreezes are not limited to these chemicals. Any chemical with low toxicity, especially natural chemicals, are suitable for this purpose. The percent content of antifreezes in ME depends on chemical properties, generally at a range of 0.1-15%, preferably at a range of 2-8%.

Co-solvents help to dissolve the active ingredients. They are generally alcohols including but not limited to C2-C7 aliphatic alcohols (e.g., ethanol, isopropanol, butanol, hexanol), ketones and esters (e.g., glyceryl triacetate, gamma-butyrolactone), which are listed in allowed substance in NOP [www.ams.usda.gov/AMSv1. O/nop, cited on Jul. 20, 2009]. However, co-solvents are not limited to these chemicals. Any chemical with low toxicity, especially natural chemicals, are suitable for this purpose. The percent content of co-solvents in ME depends on chemical properties, generally 0.1-20%, preferred to 1-15%.

A combination of surfactant would help to stabilize microemulsion. Generally, the combination includes a nonionic surfactant and an anionic surfactant or cation surfactant. Generally, hydrophile-lipophile-balance (HLB) of any surfactant combination listed in allowed substance in NOP [www.ams.usda.gov/AMSv1. O/nop, cited on Jul. 20, 2009] falls within 13 to 40 is suitable for this purpose. These surfactants, for example, include but are not limited sulfate salt, phosphate salt, ethoxylated alcohols, ethoxylated fatty acid esters, ethoxylate phenols, ethoxylated fatty acids and so on. In a particular embodiment, the surfactant is at least one of 2-[2-[3,4-bis(2-methoxyethoxy)oxolan-2-yl]-2-(2-methoxyethoxy)ethoxy]ethyl hexadecanoate or sodium lauryl sulfate. The amount of the combined surfactants follows a range of 0.1-50%, preferably 10-40%.

Soluble Liquid or Soluble Concentrate

Soluble liquid (also referred to as "SL") (or soluble concentrate, also referred to as "SC") is a uniform liquid formulation. Active ingredient(s) is (are) dissolved in a liquid solvent (especially in water) with/without the aid of co-solvents and surfactants. The concentrate is then diluted with water when applied. Most of the anthraquinone derivatives (e.g., physcion, emodin, chrysophanol, ventiloquinone) used in the composition of the present invention possess one or multiple hydroxyl group on aromatic rings, which make the deprotonation easily under a basic condition. After forming salts, these anthraquinone derivatives would possess higher water solubility. Deprotonized anthraquinone derivatives such as emodin and physcion are still very active and they are stable in basic conditions. The content of the active ingredient (s) follows a range of about 0.001-80%, preferably 0.01-45%, more preferably about 0.02-25%.

The bases include but are not limited to carbonate salts (e.g., sodium carbonate, potassium carbonate etc), hydroxide salts (e.g., sodium hydroxide, potassium hydroxide and so on). Any allowed basic chemical allowed to use by NOP [www.ams.usda.gov/AMSv1. O/nop, cited on Jul. 20, 2009] that can deprotonate phenol hydroxyl group or form a salt with them will meets this purpose. The content of the base follows a range of about 0.1-10%, preferably about 0.2-5%.

Co-solvents for such a formulation are water miscible solvents such as alcohols (e.g., ethanol, isopropanol), acids (e.g., acetic acid, propanoic acid) and lactones (e.g., gammalactone). In a particular embodiment, it is a C2-C7 alcohol or glycol. Any water miscible solvents listed in NOP [www.ams.usda.gov/AMSv1. O/nop, cited on Jul. 20, 2009] are suitable for this purpose. The content of the co-solvent follows a range of about 0.1-20%, preferably about 0.1-15%.

Surfactants may be any dispersant allowed to use by NOP [www.ams.usda.gov/AMSv1. O/nop, cited on Jul. 20, 2009]. The dispersant includes but is not limited to humic acid, Vanisperse CB and so on. Surfactants for such a formulation can be those with high HLB values, generally over 12, preferably over 13. Any surfactants allowed to use by NOP [www.ams.usda.gov/AMSv1. O/nop, cited on Jul. 20, 2009] are suitable for such a purpose. These surfactants, for example, include but are not limited sulfate salt, phosphate salt, ethoxylated alcohols, ethoxylated fatty acid esters, ethoxylate phenols, ethoxylated fatty acids and so on. The amount of surfactants follows a range of 0.5-35%, preferably 3-8%.

Ready to Use (RTU)

Ready to use (also referred to as "RTU") is a formulation that is very low in concentration, used without dilution or mixing. It can be a solid (e.g., bait) or alternatively a liquid, frequently applied via a trigger sprayer bottle. Liquid RTU usually uses water as a carrier. RTU can be any one of the formulations such as ME, SL, SC and so on. The composition of such a formulation is similar to ME, SL or SC as described above.

Antimicrobial agents can prevent microorganisms from growing in the RTU during storage. Any chemical listed in allowed substance in NOP [www.ams.usda.gov/AMSv1. O/nop, cited on Jul. 20, 2009] is suitable for such purpose. For example, bicarbonate salts, carbonate salts, propionate salt, sorbate salt, benzoate and so on. The amount of the antimicrobial agents follows a range of 0.001 to 2, preferably 0.01-0.5%. Stabilizers can be any chemical listed in allowed substance in NOP [www.ams.usda.gov/AMSv1. O/nop, cited on Jul. 20, 2009] that can stabilize anthraquinone derivatives in the water. It includes but is not limited to water miscible solvents such as ethanol, or inorganic salt such EDTA or any surfactants listed in allowed substance in NOP [www.ams.usda.gov/AMSv1. O/nop, cited on Jul. 20, 2009]. The amount of the stabilizer follows a range of about 0.001 to 2%, preferably about 0.01-0.1%.

Surfactants for such a formulation can be dispersants or any surfactant with high HLB values, generally over 12, preferably over 13. Any dispersant or surfactant allowed to use by NOP [www.ams.usda.gov/AMSv1. O/nop, cited on Jul. 20, 2009] are suitable for such a purpose. These surfactants, for example, include but are not limited sulfate salt, phosphate salt, ethoxylated alcohols, ethoxylated fatty acid esters, ethoxylate phenols, ethoxylated fatty acids and so on. The amount of surfactants follows a range of 0.001-1%, preferably 0.01-0.5%.

Water Soluble Powder (WSP)

WSP is a powdered concentrate that can directly dissolve in water and result in spraying solution. Plant extracts containing anthraquinone derivatives may be formulated in a similar manner as with soluble liquid (SL) formulation except that solid carriers instead of water miscible co-solvent are used. Solid carriers are water soluble such as bicarbonate, carbonate and dextrins.

Water Dispersible Granules (WDG) and Water Dispersible Tablet (WGT)

These are the formulations that use carriers (e.g., kaolin, light calcium, white carbon black, silica soil algae) to absorb or stick the active ingredients, and use dispersants and other adjuvants to help disperse in water, resulting in spraying solution.

Emulsifiable Concentrate (EC)

This is a liquid concentrated form of pesticide that is mixed with water to create a spraying solution. When anthraquinone derivatives from plants are extracted with hydrophobic solvents listed in allowed substance by NOP [http://www.ams.usda.gov/AMSv1. O/nop, cited on Jul. 20, 2009], the extracts can be formulated as EC. Hydrophobic solvents include but are not limited to butanol, hexanol and ethyl acetate as well.

EXAMPLES

The examples below are presented to describe preferred embodiments and utilities of the invention and is not meant to limit the invention unless otherwise stated in the claims appended hereto.

Example 1: Soluble Concentrate

Preparation of 5% *Reynoutria sachalinensis* SC product (hereinafter referred to as "5% MBI SC product": A) 50 gram of dry knotweed (*Reynoutria sachalinensis*) ethanol extract is homogenized in 100 gram of denatured ethanol at 600 rpm for at least 5 min; B) 378 gram of calcium nitrate is homogenized in 463 grams water for at least 5 min at 600 rpm; C) A and B are combined and then the mixture is homogenized at 2500 rpm for at least 5 min. At the end, the temperature of final formulation was about 44-50° C.

Evaluation of Physical properties of 5% *Reynoutria sachalinensis* SC: Dispersion and stability of new 5% SC was evaluated at 200-fold dilution with standard hard water (note: 200-fold dilution is recommended application rate). There was negligible insoluble precipitate (<1% of the total dry solid). Storage test at 4° C. and 54° C. for 2 weeks showed that there was a small layer of precipitates under the bottle, but this layer would be suspended again by slightly shaking the bottle. However, unlike the 5% *Reynoutria sachalinensis* SC, prepared using procedures described in U.S. Pat. No. 5,989,429 and marketed as MILSANA® biofungicide from KHH there was no aggregation and no big particles observed. There was no nozzle blockage when applied with 5% MBI SC product.

Cucumber powdery mildew bioassay: The cucumber plants were 2-week old when treated. The first true open leaf was actively growing in all plants. MILSANA® biofungicide from KHH at 200-fold dilution was used as a positive control. Five different batches of 5% REGALIA® SC biofungicide samples were evaluated at 200-fold dilution. Treatments were prepared in water containing 0.02% (v/v) Nu-Film P. Treatments were applied using a 2 oz mist sprayer. Each plant was treated 3.5-4 ml (2.5-3 ml for upper side and 1 ml for lower side). Three hours after treatment, all plants were inoculated with a fresh conidial suspension of approximately 8.4 X105 conidia per ml suspended in water. The number of powdery mildew lesions was determined 7 days after treatment/inoculation.

Comparison of bioassay results: Results (Table 1) indicated that average efficacy of 5% MBI SC product SC was much higher than that of 5% MILSANA® SC biofungicide. In addition, efficacy of 5% MBI SC product SC was reproducible through batch to batch.

TABLE 1

Comparison of efficacy between 5% MILSANA ® SC
biofungicide and 5% REGALIA ® SC biofungicide
toward cucumber powdery mildew *Sphaerotheca fuliginea*

| Treatments | Colony/leaf* | Control (%) |
|---|---|---|
| Untreated control | 196.0 ± 47.2 | 0 |
| MILSANA ® SC biofungicide | 33.0 ± 11.7 | 83.2 |
| MBI SC product sample 1 | 7.3 ± 4.3 | 96.3 |
| MBI SC product sample 2 | 7.3 ± 1.1 | 96.3 |
| MBI SC product sample 3 | 5.5 ± 2.9 | 97.2 |
| MBI SC product sample 4 | 4.0 ± 2.1 | 98.0 |
| MBI SC product sample 5 | 1.0 ± 0.7 | 99.5 |

Example 2: Microemulsion (Hereinafter Referred to as "ME")

Preparation of 5% *Reynoutria sachalinensis* ME (hereinafter referred to as 5% MBI ME Product): 1) 5 gram of dry knotweed (*Reynoutria sachalinensis*) ethanol extracts are mixed with 2 gram hexanol and 2 gram propylene glycol at 900 rpm for 5 minutes; 2) 22 gram of 2-[2-[3,4-bis(2-methoxyethoxy)oxolan-2-yl]-2-(2-methoxyethoxy)ethoxy] ethylhexadecanoate and 3 gram sodium lauryl sulfate are added to the mixture and mixed at 900 rpm for 5 minutes; 3) 3 gram of calcium propionate is mixed with 63 gram of water; 4) The mixture from the step 3 is added to the mixture from step 2 by stirring at 900 rpm for 10 minutes to form a clear formulations. This formulation meets the dispersion and stability test, and also passed 2-week storage stability test at both 4 and 54° C.

Preparation of 20% *Reynoutria sachalinensis* ME (hereinafter referred to as 20% MBI ME Product): 1) 20 gram of dry knotweed (*Reynoutria sachalinensis*) ethanol extract is mixed with 7 gram hexanol and 4 grams propylene glycol at 900 rpm for 5 minutes; 2) 30 gram of 2-[2-[3,4-bis(2-methoxyethoxy)oxolan-2-yl]-2-(2-methoxyethoxy)ethoxy] ethyl hexadecanoate and 6 gram sodium lauryl sulfate is added to the mixture and all of the ingredients are mixed at 900 rpm for 5 minutes; 3) 6 gram of potassium sorbate is mixed with 27 gram of water; 4) the mixture from the step 3 is added into the mixture from the step 2 by stirring at 900 rpm for 10 minutes to form a clear formulation. This formulation meets the dispersion and stability test, and also passed 2-week storage stability test at both 4 and 54° C.

Cucumber powdery mildew bioassay: The Bioassay was performed as described above except that plants were inoculated with a conidial suspension of $2.4 \times 10^5$ conidia per ml. Two batches of 5% MBI ME Product was diluted at 200, 800 and 3200 times. One batch of 20% MBI ME Product was tested at 2000 fold dilution.

Comparison of bioassay results: Results (Table 2) indicated that average efficacy of 5% MBI ME Product at 800 fold dilution was equal to or better than that of 5% MILSANA® SC biofungicide at 200-fold dilution. Similarly, average efficacy of 20% MBI ME Product at 2000 fold dilution (Table 3) was equal to or better than that of 5% MILSANA® SC biofungicide at 200-fold dilution.

TABLE 2

Comparison of efficacy between 5% MILSANA ® SC biofungicide 5% MBI ME Product toward cucumber powdery mildew *Sphaerotheca fuliginea*

| Treatment | dilution | Lesions | % control |
|---|---|---|---|
| Control | — | 381.7 | 0 |
| 5% MILSANA ® SC biofungicide | 200 | 98.3 | 74.2 |
| 5% MBI ME Product (I) | 200 | 14.0 | 95.8 |
| 5% MBI ME Product (I) | 800 | 56.7 | 83.5 |
| 5% MBI ME Product (I) | 3200 | 280.0 | 32.7 |
| 5% MBI ME Product (II) | 200 | 7.7 | 97.9 |
| 5% MBI ME Product (II) | 800 | 83.3 | 78.4 |
| 5% MBI ME Product (II) | 3200 | 210.0 | 43.9 |

TABLE 3

Comparison of efficacy between 5% MILSANA ® SC biofungicide 20% MBI ME Product toward cucumber powdery mildew *Sphaerotheca fuliginea*

| Treatment | dilution | Average lesions | % control |
|---|---|---|---|
| Control | — | 388.0 | 0 |
| 5% MILSANA ® SC biofungicide | 200 | 12.0 | 96.6 |
| 20% MBI ME Product | 2000 | 8.3 | 97.4 |

Example 3: Soluble Liquid (SL)

Preparation of 20% MBI SL Product: 1) 2 gram sodium hydroxide (or 5 gram sodium carbonate) is dissolved into 50 grams of water with 4 gram of propylene glycol; 2) 5 gram of liquid formic acids is added to dissolve; 3) 20 gram of dry knotweed (*Reynoutria sachalinensis*) ethanol extracts is added slowly with stirring at 900 rpm until a uniform solution is obtained. This formulation meets the dispersion and stability test, and also passed 2-week storage stability test at both 4 and 54° C. The pH value of such a formulation is around 8-8.5.

Cucumber powdery mildew bioassay: Bioassay was performed as described above except that plants were inoculated with a conidial suspension of $5 \times 10^5$ conidia per ml. Four batches of 20% MBI SL Product was diluted at 2000 times.

Comparison of bioassay results: Results (Table 4) indicated that average efficacy of 20% MBI SL Product at 2000 fold dilution was equl to or better than that of 5% MILSANA® SC biofungicide at 200-fold dilution.

TABLE 4

Comparison of efficacy between 5% MILSANA ® SC biofungicide 20% MBI SL Product toward cucumber powdery mildew *Sphaerotheca fuliginea*

| Treatment | Dilution | Average lesions | % Control |
|---|---|---|---|
| Control | — | 388.0 | 0 |
| 5% MILSANA ® SC biofungicide | 200 | 12.0 | 96.6 |
| 20% MBI SL Product (I) | 2000 | 0.3 | 99.9 |
| 20% MBI SL Product (II) | 2000 | 0.7 | 99.8 |
| 20% MBI SL Product (III) | 2000 | 1.0 | 99.7 |
| 20% MBI SL Product (IV) | 2000 | 2.0 | 99.4 |

Example 4: Ready to Use (RTU)

Preparation of 0.025% MBI RTU-01 Product: 1) 0.25 gram dry knotweed (*Reynoutria sachalinensis*) ethanol extract is dissolved in 0.2 gram hexanol and 100 gram ethanol; 2) 0.3 gram of sodium laureth sulfate is added to the mixture, and mixed in; 3) 899.25 gram water is added to the mixture; the mixture is stirred at 900 rpm till a uniform solution is obtained. This formulation passed 2-week storage stability test at 4 and 54° C. It also did not show any phytotoxicity on many flowers Preparation of 0.025% MBI RTU-02 Product: 1) 0.25 gram dry knotweed (*Reynoutria sachalinensis*) ethanol extract is dissolved in 0.2 gram hexanol and 0.2 gram ethanol; 2) 0.09 gram of sodium laureth sulfate is added to the mixture, and mixed in; 3) 998.96 gram water is added to the mixture and mixed in as well; and 4) 0.3 gram of calcium propionate is added and mixed well by stirring at 900 rpm till a uniform solution is obtained. This formulation passed 2-week storage stability test at 4 and 54° C. It also did not show any phytotoxicity on many flowers.

Cucumber powdery mildew bioassay: Bioassay was performed as described above except that plants were inoculated with a conidial suspension of $5 \times 10^5$ conidia per ml. The same volume of 0.025% MBI RTU product was sprayed for each pot of cucumber plants as 200-fold dilution of 5% MBI ME product.

Comparison of bioassay results: Results (Table 5) indicated that average efficacy of 0.025% MBI RTU product was equal to that of 5% MILSANA® ME biofungicide at 200-fold dilution.

TABLE 5

Comparison of efficacy between 5% REGALIA ® ME biofungicide and 0.025% REGALIA ® RTU biofungicide toward cucumber powdery mildew *Sphaerothera fuliginea*

| Treatment | Dilution | Severity % | % Control |
| --- | --- | --- | --- |
| Control | — | 92.5 ± 2.9 | 0 |
| 5% MBI ME Product | 200 | 0.5 ± 0.6 | 99.5 |
| 0.025% MBI RTU Product (I) | 1 | 0.0 ± 0.0 | 100 |
| 0.025% MBI RTU Product (II) | 1 | 2.5 ± 2.9 | 97.3 |

Although this invention has been described with reference to specific embodiments, the details thereof are not to be construed as limiting, as it is obvious that one can use various equivalents, changes and modifications and still are within the scope of the present invention.

Various references are cited throughout this specification, each of which is incorporated herein by reference in its entirety.

What is claimed is:

1. A method for reducing a powdery mildew infection in a plant comprising the step of:
   applying a formulation comprising a preparation having 0.01% to 45% by weight of a root extract derived from *Reynoutria sachalinensis*, in an amount effective to induce plant resistance to phytopathogens, and an adjuvant, carrier, surfactant or diluent to the plant, in an amount effective to reduce said powdery mildew infection.

2. The method according to claim 1, wherein said surfactant is 0.01% to 15% by weight sodium lauryl sulfate.

3. The method according to claim 1, wherein said surfactant is 0.1% to 35% by weight 2-[2-[3,4-bis(2-methoxyethoxy)oxolan-2-yl]-2-(2-methoxyethoxy)ethoxy]ethyl hexadecanoate.

4. The method according to claim 1, further comprising an alcohol or diol comprising 2-7 carbons, wherein said alcohol or diol is selected from ethanol, isopropanol, butanol, hexanol, ethylene glycol and propylene glycol.

5. The method according to claim 1, further comprising 0.1% to 8% by weight propylene glycol.

6. The method according to claim 1, further comprising 0.1% to 10% by weight hexanol.

7. The method according to claim 1, further comprising 2% to 10% by weight anti-microbial agent.

8. The method according to claim 1, wherein the formulation is a liquid or micro-emulsion formulation.

9. The method according to claim 1, further comprising an antifoaming agent.

10. The method according to claim 1, wherein the formulation further comprises a chemical pesticide, biopesticide or natural or oil-product having fungicidal or insecticidal activity.

11. The method according to claim 1, wherein the preparation is 1% to 30% by weight.

\* \* \* \* \*